US008574331B2

(12) United States Patent
Bangera et al.

(10) Patent No.: US 8,574,331 B2
(45) Date of Patent: Nov. 5, 2013

(54) AIR-TREATMENT MASK SYSTEMS, AND RELATED METHODS AND AIR-TREATMENT MASKS

(75) Inventors: Mahalaxmi Gita Bangera, Renton, WA (US); Roderick A. Hyde, Redmond, WA (US); Jordin T. Kare, Seattle, WA (US); Lowell L. Wood, Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 78 days.

(21) Appl. No.: 13/317,770

(22) Filed: Oct. 26, 2011

(65) Prior Publication Data

US 2013/0104733 A1 May 2, 2013

(51) Int. Cl.

*A61L 9/20* (2006.01)
*A61M 16/06* (2006.01)
*B01D 45/04* (2006.01)
*B01D 46/10* (2006.01)

(52) U.S. Cl.

USPC ................ 55/385.1; 55/471; 55/472; 55/473; 55/DIG. 33; 55/DIG. 34; 55/DIG. 35; 96/127; 96/140; 96/417; 96/397; 96/424; 128/201.23; 128/202.22; 128/205.27; 128/206.12

(58) Field of Classification Search

USPC ................. 55/385.1, 471, 472, 473, DIG. 33, 55/DIG. 34, DIG. 35; 96/127, 140, 417, 96/397, 424; 128/201.23, 202, 22, 205.27, 128/206.12

See application file for complete search history.

(56) References Cited

U.S. PATENT DOCUMENTS 4,658,707 A * 4/1987 Hawkins et al. ................ 454/75
4,722,747 A * 2/1988 Armbruster ..................... 96/140
4,790,306 A * 12/1988 Braun et al. ............. 128/206.12
4,807,614 A * 2/1989 van der Smissen et al. .......... 128/201.23
4,886,056 A 12/1989 Simpson
4,917,862 A * 4/1990 Kraw et al. ....................... 422/4
5,004,487 A * 4/1991 Kowalczyk ..................... 96/127
5,033,465 A * 7/1991 Braun et al. ............. 128/205.27
5,165,395 A * 11/1992 Ricci ....................... 128/202.22
5,322,058 A 6/1994 Pasternack (Continued)

OTHER PUBLICATIONS

Mateen, et al.; "Air Pollution as an Emerging Global Risk Factor for Stroke" JAMA, Mar. 23/30, 2011—vol. 305, No. 12; jama.ama-assn.org; pp. 1240-1241.

(Continued)

*Primary Examiner* — Robert Clemente
*Assistant Examiner* — Minh-Chau Pham
(74) *Attorney, Agent, or Firm* — Dorsey & Whitney LLP

(57) ABSTRACT

Embodiments disclosed herein include air-treatment mask systems having at least one controllable air-treatment device that is controlled responsive to one or more signals from at least one pollutant sensor, and related methods of operation and air-treatment masks. In an embodiment, an air-treatment mask system includes a wearable air-treatment mask having a mask body including a face-securing member, and at least one controllable air-treatment device supported by the mask body. The air-treatment device is configured to treat incoming air. The system includes at least one pollutant sensor configured to sense ambient air for a presence of at least one pollutant and output one or more signals responsive to the sensing. The system includes control electrical circuitry operably coupled to the air-treatment device and the pollutant sensor and configured to control operation of the controllable air-treatment device responsive to receiving the signal(s) from the pollutant sensor.

66 Claims, 9 Drawing Sheets

(56) References Cited

U.S. PATENT DOCUMENTS

| | | | |
|---|---|---|---|
| 5,413,097 A | 5/1995 | Birenheide et al. | |
| 5,950,621 A | 9/1999 | Klockseth et al. | |
| 6,660,070 B2 * | 12/2003 | Chung et al. | 96/424 |
| 6,761,169 B2 | 7/2004 | Eswarappa | |
| 6,772,762 B2 | 8/2004 | Piesinger | |
| 6,793,702 B2 | 9/2004 | Eswarappa | |
| 7,118,608 B2 * | 10/2006 | Lovell | 55/385.1 |
| 2002/0092525 A1 | 7/2002 | Rump et al. | |
| 2004/0186339 A1 | 9/2004 | Galloway | |
| 2007/0163588 A1 | 7/2007 | Hebrank et al. | |
| 2007/0240716 A1 | 10/2007 | Marx | |
| 2010/0108071 A1 | 5/2010 | Macy, Jr. | |
| 2011/0056496 A1 | 3/2011 | Tilley et al. | |

OTHER PUBLICATIONS

Romanosky et al.; "Low Cost Miniature Multifunctional Solid-State Gas Sensors"; U.S. Department of Energy Office of Fossil Energy National Energy Technology Laboratory; Project Facts; Aug. 2007; pp. 1-2.

E2V Tecnologies; "IR15TT-R Miniature Infrared Gas Sensor for Monitoring Carbon Dioxide and Methane up to 100% volume"; Jul. 2009, Version 2; pp. 1-6.

Zhang, et al.; "Recent progress in carbon nanotube-based gas sensors"; Jul. 7, 2008; Nanotechnology 19 (2008) 332001; stacks.iop.org/Nano/19/332001; pp. 1-14.

Capone, et al.; "Solid State Gas Sensors: State of the Art and Future Activities"; Aug. 28, 2003; Journal of Optoelectonics and Advance Materials vol. 5, No. 5, 2003; pp. 1335-1348.

PCT International Search Report; International App. No. PCT/US12/62047; Jan. 9, 2013; pp. 1-2.

* cited by examiner

AIR-TREATMENT MASK SYSTEMS, AND RELATED METHODS AND AIR-TREATMENT MASKS

SUMMARY

Embodiments disclosed herein are directed to air-treatment mask systems having at least one controllable air-treatment device (e.g., an active or a passive air filter) that is controlled responsive to one or more signals from at least one pollutant sensor encoding pollutant data, and related methods of operation and air-treatment masks. In an embodiment, an air-treatment mask system includes a wearable air-treatment mask including a face-securing member, and at least one controllable air-treatment device supported by the mask body. The at least one controllable air-treatment device is configured to treat incoming air. At least one pollutant sensor is provided, which is configured to sense ambient air for a presence of at least one air pollutant therein and output one or more signals responsive to the sensing. Control electrical circuitry is operably coupled to the at least one controllable air-treatment device and the at least one pollutant sensor. The control electrical circuitry is configured to control the operation of the at least one controllable air-treatment device responsive to receiving the one or more signals from the at least one pollutant sensor.

In an embodiment, a wearable air-treatment mask includes a mask body including a face-securing member, and at least one controllable air treatment device supported by the mask body. The at least one controllable air treatment device is configured to controllably treat incoming air. The wearable air-treatment mask includes at least one pollutant sensor configured to sense ambient air for a presence of at least one pollutant therein and further configured to output one or more signals responsive to the sensing. Control electrical circuitry is operably coupled to the at least one controllable air treatment device and the at least one pollutant sensor. The control electrical circuitry is configured to control operation of the at least one controllable air treatment device responsive to receiving the one or more signals from the at least one pollutant sensor.

In an embodiment, a method of treating ambient air to be breathed by a user is disclosed. The method includes sensing at least one pollutant in the ambient air to be breathed by the user using at least one pollutant sensor. The method further includes, responsive to the sensing the at least one pollutant, treating incoming air using at least one controllable air-treatment device of a wearable air-treatment mask.

In an embodiment, a method of operating at least one controllable air-treatment device of a wearable air-treatment mask worn by a user is disclosed. The method includes sensing at least one pollutant in ambient air to be breathed by the user with at least one pollutant sensor. The method further includes, responsive to the sensing the at least one pollutant, modifying operation of the at least one controllable air-treatment device of the wearable air-treatment mask.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
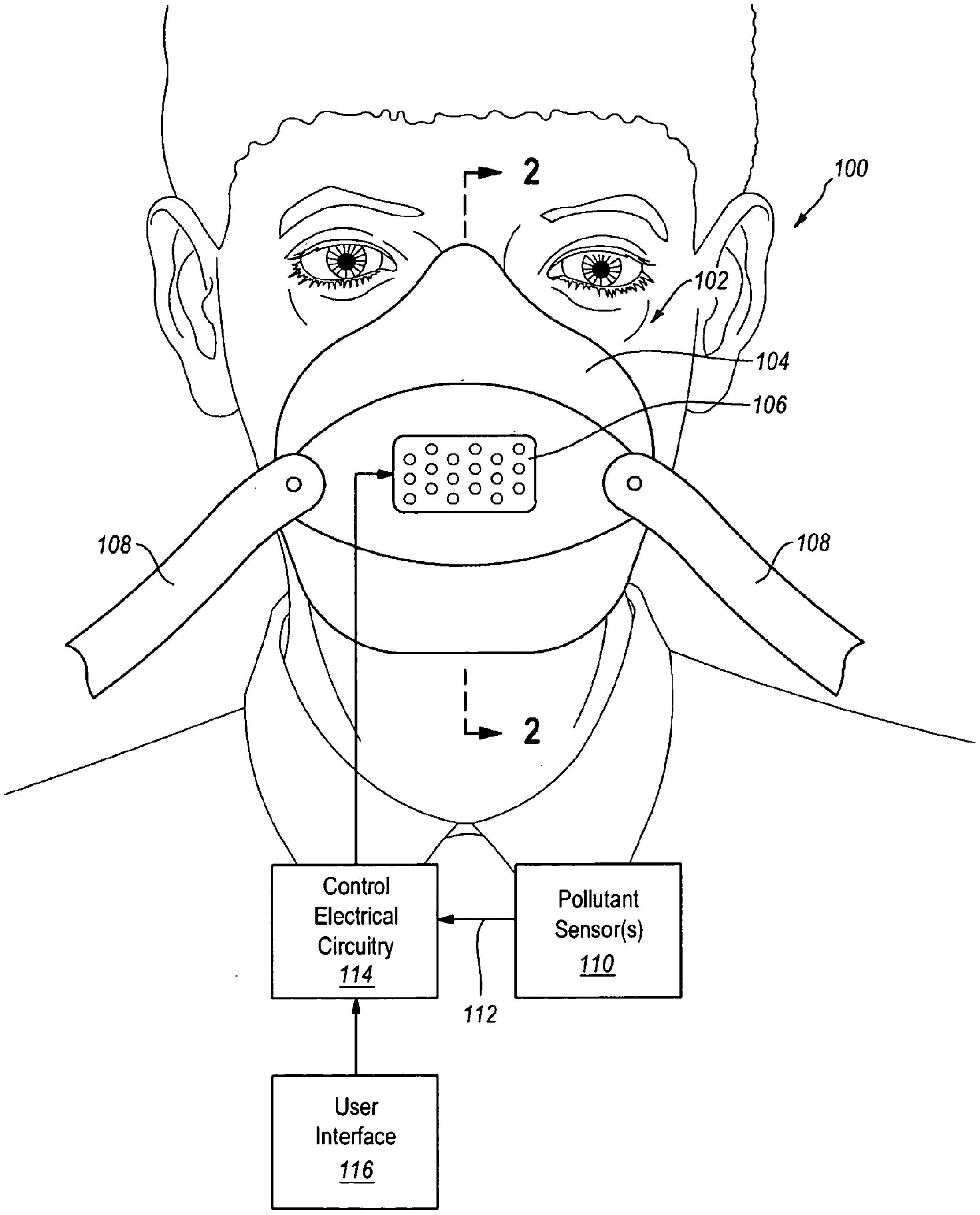
FIG. 1 is a schematic plan view of an embodiment of an air-treatment mask system including a wearable air-treatment mask.

Embodiments disclosed herein are directed to air-treatment mask systems having at least one controllable air-treatment device (e.g., an active or a passive air filter) that is controlled responsive to one or more signals from at least one pollutant sensor encoding pollutant data, and related methods of operation and air-treatment masks. The disclosed air-treatment mask systems may be portable and easy to use, while also protecting the user from breathing noxious chemicals or particulate pollutants in ambient air and, additionally, may be specifically configured or configurable to treat (e.g., filter or at least partially neutralize) ambient air of one or more selected air pollutants.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 is a schematic plan view of an embodiment of an air-treatment mask system 100. The air-treatment mask system 100 includes a wearable air-treatment mask 102 having a mask body 104 configured to be worn by a user and generally conform to the user's face. The air-treatment mask system 100 further includes at least one controllable air-treatment device 106 that is supported by the mask body 104. The at least one controllable air-treatment device 106 is positioned and configured to treat (e.g., filter or at least partially neutralize) ambient air for transformation to treated incoming air. A variety of different types of air-treatment devices (e.g., passive and active air filters) may be employed for the at least one controllable air-treatment device 106, and will be discussed in more detail below. In an embodiment, the controllable air-treatment device 106 is configured to perform at least one of filtering, at least partial neutralizing, or at least partial sterilizing the ambient air for transformation to treated incoming air that the user breathes. In use, the user is able to breathe treated incoming air through at least one controllable air-treatment device 106 drawn from the ambient air surrounding the user and the wearable air-treatment mask 102.

The mask body 104 may exhibit any suitable configuration. For example, the mask body 104 may be made from a suitable fabric, plastic, or combination thereof that is sufficiently rigid to support the at least one air-treatment deice 106 and sufficiently flexible to comfortably conform to the user's face. Straps 108 are shown in the illustrated embodiment as being attached to the mask body 104 for carrying the wearable air-treatment mask 102 and securing the mask body 104 on the user's head. However, other types of face-securing members may be employed besides the straps 108 shown in FIG. 1.

The air-treatment mask system 100 further includes at least one pollutant sensor 110 exposed to the ambient air and configured to sense at least one air pollutant in the ambient air and output one or more signals 112 encoding the pollutant data responsive to sensing the air pollution. For example, the at least one air pollutant to be sensed may include at least one of one or more types of airborne particles (e.g., dust, pollen, or aerosols), or one or more types of chemical pollutants. The one or more types of chemical pollutants may include, for example, at least one of ozone ($O_3$), nitrogen oxide ($NO_x$), sulfur oxide ($SO_2$), carbon monoxide (CO), or one or more types of pathogens.

The at least one pollutant sensor 110 may be selected from a number of different pollutant sensors. For example, the at least one pollutant sensor 110 may include one or more solid-state pollutant gas sensors configured to measure a concentration of $CO_x$ (e.g., CO), $NO_x$, $SO_x$ (e.g., $SO_2$), or other type of gas in the ambient air. Such solid-state pollutant gas sensors may be ceramic electrochemical gas sensors, semiconductor gas sensors (e.g., chemoresistive gas sensors), carbon-nanotube-based gas sensors, or other suitable sensors. Other suitable pollutant sensors for the at least one pollutant sensor 110 include sensors that detect specific gases or particulates in the ambient air using optical techniques, such as spectroscopy (e.g., luminescence, phosphorescence, fluorescence, Raman, etc.), ellipsometry, interferometry (e.g., white light interferometry, modal interferometry in optical waveguide structures), spectroscopy of guided modes in an optical waveguide structure such as grating couplers or resonant mirrors, surface plasmon resonance, or another suitable technique. It is noted that the at least one pollutant sensor 110 may employ at least one, two, or any combination of any of the foregoing types of pollutant sensors, as desired or needed for a particular application environment.

The air-treatment mask system 100 further includes control electrical circuitry 114 that is operably coupled to both the at least one pollutant sensor 110 and the controllable air-treatment device 106. For example, the control electrical circuitry 114 may be operably coupled to both the at least one pollutant sensor 110 and the at least one controllable air-treatment device 106 via at least one of an electrical connection, an optical connection, or a wireless connection. The control electrical circuitry 114 is configured to control the operation of the at least one controllable air-treatment device 106 at least partially based on the one or more signals 112 received from the at least one pollutant sensor 110. Although not shown, a battery or other electrical power source may power the at least one pollutant sensor 110, the control electrical circuitry 114, and the at least one controllable air-treatment device 106 when it is an active air-treatment device.

In the illustrated embodiment, a user interface 116 (e.g., a computer touchscreen, keypad, or other computing device, etc.) for inputting user input is provided, which may be operably coupled to the control electrical circuitry 114. The user interface 116 enables the user to select specific operational characteristics by which the at least one controllable air-treatment device 106 is controlled. However, it should be noted that in any of the embodiments disclosed herein, the user interface 116 may be omitted and the control electrical circuitry 114 may be pre-programmed without user input, for example, via software, firmware, programmable logical devices, or other technique to control the at least one controllable air-treatment device 106 in a selected manner.

In operation, the at least one pollutant sensor 110 senses a presence or absence of the at least one air pollutant in the ambient air and outputs the one or more signals 112 to the control electrical circuitry 114. Based on the information encoded in the one or more signals 112, the control electrical circuitry 114 controls the operation of the at least one controllable air-treatment device 106. In an embodiment, the control electrical circuitry 114 selectively activates the at least one controllable air-treatment device 106 responsive to the one or more signals 112 indicating that the at least one air pollutant is above a threshold pollutant concentration level. In an embodiment, the control electrical circuitry 114 selectively activates the at least one controllable air-treatment device 106 responsive to the one or more signals 112 indicating that the at least one air pollutant contains certain types of airborne pollutants, such as certain types of chemical pollutants or certain types of airborne particles. In an embodiment, the threshold pollutant concentration level is determined according to limitations or restrictions of the user (e.g., it can be customized based on a user's particular needs or health condition). For example, in an embodiment, the at least one controllable air-treatment device 106 or system 100 described herein is configured for personalization of which pollutants, what activation threshold, etc.

As discussed above, the user interface 116 enables the user to select specific operational characteristics by which the at least one controllable air-treatment device 106 is controlled. In an embodiment, the user interface 116 and the control electrical circuitry 114 may be configured so that the user can select the threshold pollutant concentration level above which the control electrical circuitry 114 activates that the at least one controllable air-treatment device 106. In an embodiment, the user interface 116 and the control electrical circuitry 114 may be configured so that the user can select which certain types of airborne pollutants will cause the control electrical circuitry 114 to activate the at least one controllable air-treatment device 106.

In an embodiment, the control electrical circuitry 114 and the at least one pollutant sensor 110 may be physically integrated with the mask body 104. For example, the control electrical circuitry 114 and the at least one pollutant sensor 110 may be mounted on an inside or an exterior of the mask body 104. In an embodiment, the at least one pollutant sensor 110 may be wearable by the user (e.g., in a pouch) and in communication with the control electrical circuitry 114 which maybe physically integrated with the mask body 104. In an embodiment, the control electrical circuitry 114 may be physically integrated with the mask body 104, while the at least one pollutant sensor 110 is remote from the air-treatment mask system 100 and in wirelesss communication with the control electrical circuitry 114. For example, the at least one pollutant sensor 110 may be located in a room, a building, along a street, or other suitable place, but still in wireless communication with the control electrical circuitry 114 either directly or indirectly via another device such as a cell phone. In an embodiment, both the control electrical circuitry 114 and the at least one pollutant sensor 110 are remote from the air-treatment mask system 100, with the control electrical circuitry 114 in wirelesss communication with the at least one controllable air-treatment device 106 for controlling the operation thereof.

Figure 2A:
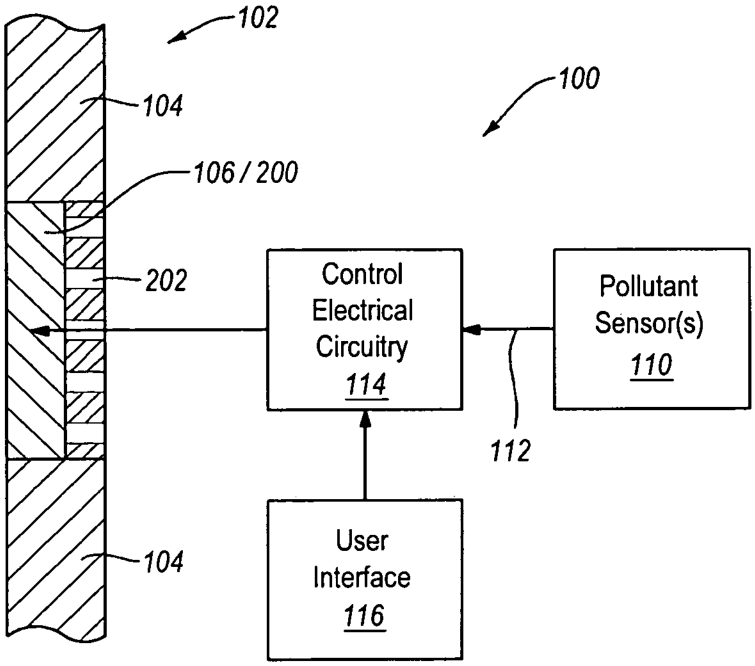
FIG. 2A is a schematic partial cross-sectional view of an embodiment of the air-treatment mask system shown in FIG. 1 taken along line 2-2 thereof in which the at least one controllable air-treatment device is configured as an active air filter.

FIG. 2A is a schematic partial cross-sectional view of an embodiment of the air-treatment mask system 100 in which the at least one controllable air-treatment device 106 is configured as an active air filter 200. The active air filter 200 may be configured as at least one of an electrostatic filter or a chemical-active filter. The mask body 104 may include a plurality of vents 202 in fluid communication with the active air filter 200 so that ambient air surrounding the wearable air-treatment mask 102 flows through the vents 202 to the active air filter 200 when the user attempts to breathe the incoming air.

In operation, the user attempts to breathe the ambient air surrounding the wearable air-treatment mask 102, thereby causing the ambient air to flow through the vents 202 to the active air filter 200 to become filtered incoming air that the user breathes. When the active air filter 200 is activated by the control electrical circuitry 114 responsive to pollutant sensing by the at least one pollutant sensor 110, the ambient air that is flowed to the active air filter 200 is filtered by it and the filtered incoming air is delivered to the user for breathing. When the active air filter 200 is not activated by the control electrical circuitry 114, the user may simply breather unfiltered ambient air through the vents 202 and the active air filter 200.

The control electrical circuitry 114 may control the active air filter 200 as previously described with respect to FIG. 1. For example, the control electrical circuitry 114 may selectively activate the active air filter 200 responsive to the one or more signals 112 indicating that the at least one air pollutant is above a threshold pollutant concentration level, or the control electrical circuitry 114 may selectively activate active air filter 200 responsive to the one or more signals 112 indicating that ambient air contains certain types airborne pollutants, such as certain types of chemical pollutants or certain types of airborne particles.

In an embodiment, the control electrical circuitry 114 may control specific filtering operational characteristics of the active air filter 200 in addition to the control electrical circuitry 114 being configured to selectively activate the active air filter 200 responsive to the one or more signals 112. For example, the control electrical circuitry 114 may be configured to vary the filtration strength of the active air filter 200, vary an air flow rate through the active air filter 200 delivered to the user, or filter the air to be breathed by the user with the active air filter 200 to a selected air pollutant level (e.g., a selected pollutant concentration).

As discussed above, the user interface 116 enables the user to select specific operational characteristics by which the active air filter 200 operates. In an embodiment, the user interface 116 and the control electrical circuitry 114 may be configured so that the user can select the filtration strength of the active air filter 200, the air flow rate through the active air filter 200, or the selected air pollutant level to which the active air filter 200 filters the air to be breathed by the user.

Figure 2B:
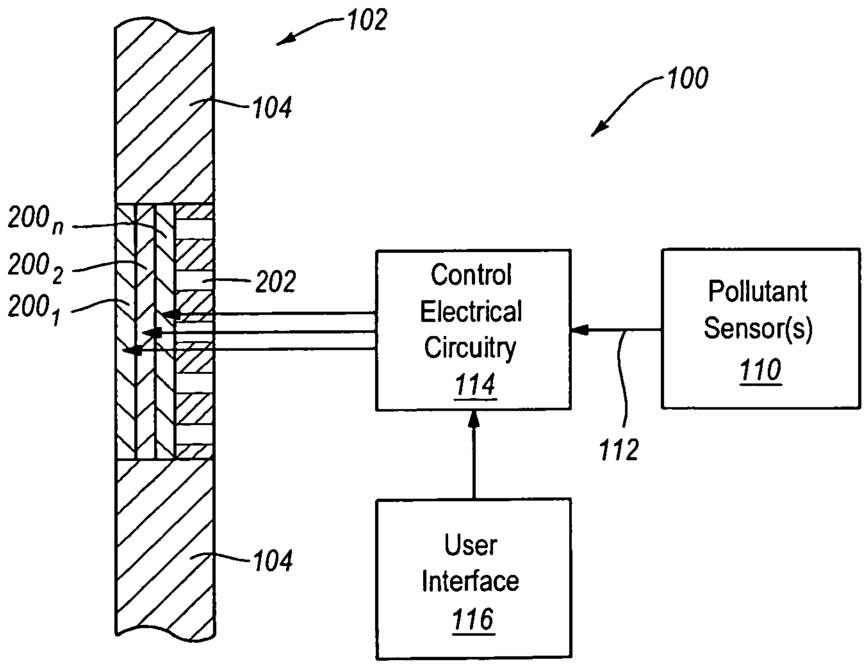
FIG. 2B is a schematic partial cross-sectional view of an embodiment of the air-treatment mask system shown in FIG. 1 taken along line 2-2 thereof in which the at least one controllable air-treatment device includes a plurality of active air filters in series with each other.

Referring to the schematic partial cross-sectional view shown in FIG. 2B, in an embodiment, a plurality of active air filters $\mathbf{200}_1$-$\mathbf{200}_n$ arranged in series are provided. Each active air filter $\mathbf{200}_1$-$\mathbf{200}_n$ may be operably coupled to the control electrical circuitry 114 and independently controllable by the control electrical circuitry 114. Each active air filter $\mathbf{200}_1$-$\mathbf{200}_n$ may be configured to selectively filter a different air pollutant. For example, one of the active air filters $\mathbf{200}_1$-$\mathbf{200}_n$ may be configured to filter certain particulates, while one of the active air filters $\mathbf{200}_1$-$\mathbf{200}_n$ may be configured to filter certain chemicals (e.g., $O_3$, $NO_x$, or $SO_x$). The control electrical circuitry 114 may be configured to selectively activate a specific one or more of the active air filters $\mathbf{200}_1$-$\mathbf{200}_n$ at least partially based on the one or more signals 112. In an embodiment, the control electrical circuitry 114 may control specific filtering operational characteristics of the active air filters $\mathbf{200}_1$-$\mathbf{200}_n$ in addition to the control electrical circuitry 114 being configured to selectively activate one or more of the active air filters $\mathbf{200}_1$-$\mathbf{200}_n$ responsive to the one or more signals 112 indicating the presence in the ambient air of one or more specific pollutants that the selected one or more of the active air filters $\mathbf{200}_1$-$\mathbf{200}_n$ are configured to filter. For example, the control electrical circuitry 114 may be configured to vary the filtration strength of one or more of the active air filters $\mathbf{200}_1$-$\mathbf{200}_n$, vary the incoming air flow through the stack of the active air filters $\mathbf{200}_1$-$\mathbf{200}_n$ delivered to the user, or filter the incoming air to be breathed by the user with the stack of the active air filters $\mathbf{200}_1$-$\mathbf{200}_n$ to a selected air pollutant level (e.g., a selected pollutant concentration). In an embodiment, a filtration path length may be controlled by selectively activating one or more of the active air filters $\mathbf{200}_1$-$\mathbf{200}_n$. For example, when all of the active air filters $\mathbf{200}_1$-$\mathbf{200}_n$ are active, a relatively longer filtration path is provided compared to when fewer ones of the active air filters $\mathbf{200}_1$-$\mathbf{200}_n$ are active which provides a shorter filtration path length.

Figure 3:
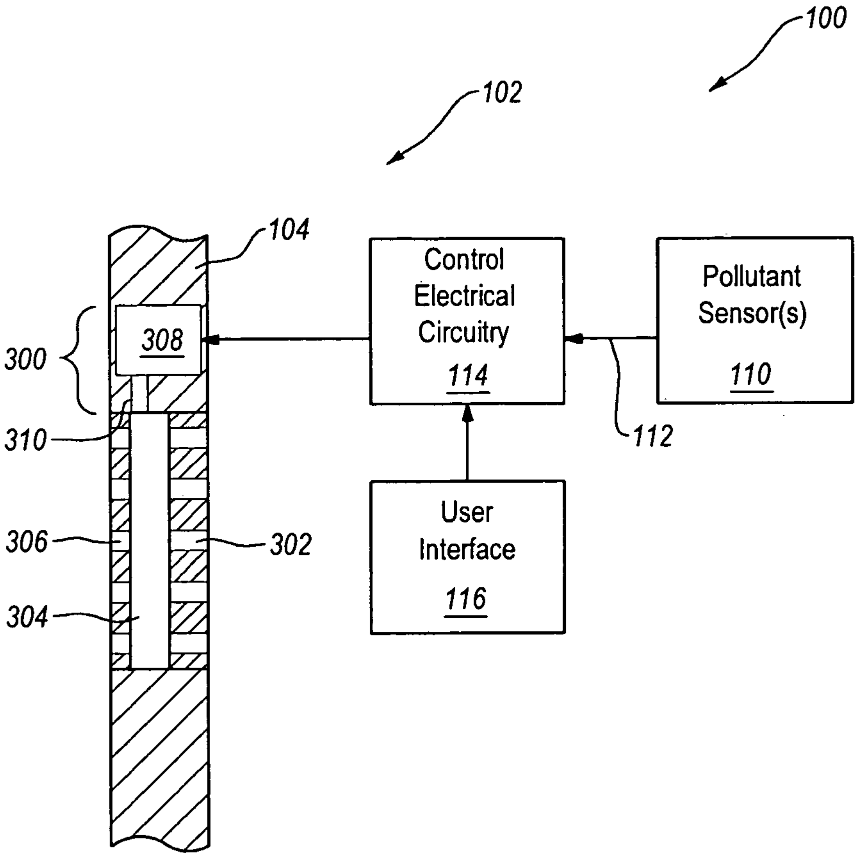
FIG. 3 is a schematic partial cross-sectional view of an embodiment of the air-treatment mask system shown in FIG. 1 taken along line 2-2 thereof in which the at least one controllable air-treatment device is configured as an active air-treatment device.

FIG. 3 is a schematic partial cross-sectional view of an embodiment of the air-treatment mask system 100 in which the at least one controllable air-treatment device 106 is configured as an active controllable air-treatment device 300. The active controllable air-treatment device 300 may be configured as an optical filter, such as at least one of a laser, a light-emitting diode (LEDs), or a lamp. The mask body 104 may include a plurality of vents 302 in fluid communication with an internal air chamber 304 that is further in fluid communication with a plurality of vents 306 so that ambient air surrounding the wearable air-treatment mask 102 flows through the vents 302, through the internal air chamber 304, and through the vents 304 when the user attempts to breathe the incoming air.

The active controllable air-treatment device 300 may include a light source 308, such as one or more lasers, one or more LEDs, or a lamp that outputs light at a selective wavelength or range of wavelengths through a waveguide 310 (e.g., an optical fiber) through which the light output by the light source 308 is delivered to the internal air chamber 304 to irradiate the incoming air therein to be breathed by the user. For example, infrared or ultraviolet wavelength light is suitable to partially neutralize or destroy many common airborne pathogens. In an embodiment, the waveguide 310 may be omitted and the light source 308 may directly output the light to the internal air chamber 304. The active controllable air-treatment device 300 may be well suited for at least partially or completely neutralizing (e.g., sterilizing) airborne pathogens that are present in the incoming air, such as spores, germs, or viruses (e.g., flu viruses). Although not shown, a battery or other electrical power source may power the at least one pollutant sensor 110, the control electrical circuitry 114, and the light source when it is an active air-treatment device.

In operation, the user attempts to breathe the ambient air surrounding the wearable air-treatment mask 102, thereby causing the ambient air to flow through the vents 302 and into the internal air chamber 304 as incoming air. In an embodiment, the incoming air is ambient air that is treated by the controllable air-treatment device 300, and is breathed by the user. The control electrical circuitry 114 directs the light source to output light that is delivered to the internal air chamber 304 through the waveguide 310 to irradiate and partially or substantially completely neutralize airborne pathogens in the ambient air flowing through the internal air chamber 304 to thereby result in at least partially neutralized incoming air for breathing by the user. The at least partially neutralized incoming air passes through the vents 306 for breathing by the user.

The control electrical circuitry 114 may control the active controllable air-treatment device 300 as previously described with respect to FIG. 1. For example, the control electrical circuitry 114 may selectively activate the active controllable air-treatment device 300 to output the light responsive to the one or more signals 112 indicating that the pathogens are present in the ambient air above a threshold pollutant concentration level, or the control electrical circuitry 114 may selectively activate active air filter 200 responsive to the one or more signals 112 indicating that the ambient air contains certain types airborne pollutants, such as certain types pathogens.

As discussed above, the user interface 116 enables the user to select specific operational characteristics by which the active controllable air-treatment device 300 operates. In an embodiment, the user interface 116 and the control electrical circuitry 114 may be configured so that the user can select the intensity of the light output by the light source 308, the threshold pollutant concentration level above which the light source 308 irradiates the air, or the selected air pollutant level to which the active controllable air-treatment device 300 filters the air to be breathed by the user.

Figure 4:
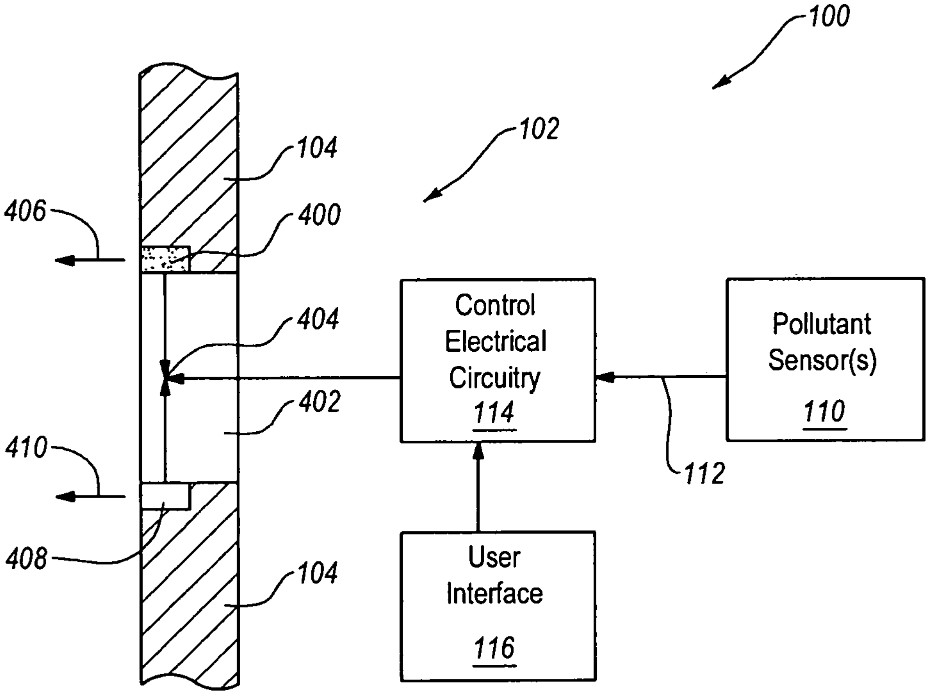
FIG. 4 is a schematic partial cross-sectional view of an embodiment of the air-treatment mask system shown in FIG. 1 taken along line 2-2 thereof in which the at least one controllable air-treatment device is configured as a passive air filter.

FIG. 4 is a schematic partial cross-sectional view of an embodiment of the air-treatment mask system 100 in which the at least one controllable air-treatment device 106 is configured as a passive air filter 400. For example, the passive air filter 400 may include at least one of a fibrous filter (e.g., a HEPA filter), activated charcoal, or a zeolite-based filter. The wearable air-treatment mask 102 includes a port 402 through which ambient air may pass as incoming air to at least one valve 404 responsive to the user breathing. For example, the at least one valve 404 may be an electronically actuated valve. The at least one valve 404 may selectively direct the incoming air to the passive air filter 400, which is filtered upon passing therethrough, so that treated incoming air 406 is delivered to the user. The at least one valve 404 may also selectively direct the ambient air passing through the port 402 to a port 408 through which the ambient air 410 is delivered to the user in an unfiltered condition. Although not shown, a battery may power the at least one pollutant sensor 110, the control electrical circuitry 114, and the at least one valve 404.

In operation, initially, the at least one valve 404 may be in a configuration so that the user can draw the ambient air through either the passive air filter 400 or the port 408, becoming incoming air to be breathed by the user. The user attempts to breathe the ambient air surrounding the wearable air-treatment mask 102 to thereby cause the ambient air to flow through the port 402 to the at least one valve 404. The control electrical circuitry 114 selectively directs the at least one valve 402 to allow the incoming air to flow to the passive air filter 400 for filtering operations responsive to the one or more signals 112 output by the at least one pollutant sensor 110. For example, the control electrical circuitry 114 may selectively control the at least one valve 404 to allow the received incoming air to flow to the passive air filter 400 responsive to the one or more signals 112 indicating that pollutants (e.g., chemical or particulate pollutants) are present in the ambient air above a threshold pollutant concentration level, or the control electrical circuitry 114 selectively opens the at least one valve 404 to allow the received incoming air to flow to the passive air filter 400 responsive to the one or more signals 112 indicating that the ambient air contains certain types airborne pollutants, such as certain types pathogens. If the one or more signals 112 output by the at least one pollutant sensor 110 indicates that the ambient air is substantially free of airborne pollutants (e.g., select airborne pollutants) or the airborne pollutants are below a threshold pollutant concentration level, the control electrical circuitry 114 may selectively control the at least one valve 404 to allow the incoming air to flow through the port 408 to the user for breathing unfiltered or alternatively may not activate the at least one valve 404 to allow the incoming air to pass to the passive air filter 400 as applicable.

The user interface 116 enables the user to select specific operational characteristics by which the at least one valve 404 operates. In an embodiment, the user interface 116 and the control electrical circuitry 114 may be configured so that the user can select a threshold pollutant concentration level above which the control electrical circuitry 114 controls the at least one valve 404 to direct incoming air to the passive air filter 400. In an embodiment, the user interface 116 and the control electrical circuitry 114 may be configured so that the user can select which certain types of airborne pollutants will cause the control electrical circuitry 114 to control the at least one valve 404 so that incoming air is directed to the passive air filter 400.

In an embodiment, the control electrical circuitry 114 may control how much of the incoming air is directed to the passive air filter 400 and filtered by the passive filter 400. For example, in an embodiment, is a partial bypass (e.g., 60% by volume) of the incoming air is directed through the passive air filter 400, while the balance of the ambient air (e.g., 40% by volume) passes through the port 408. In an embodiment, the at least one valve 404 may control what type of filter the incoming air is flowed through. For example, the passive air filter 400 may include multiple passive or active air filters, and the control electrical circuitry 114 may control the at least one valve 404 to direct the incoming air to a selected one of the multiple filters.

Figure 5:
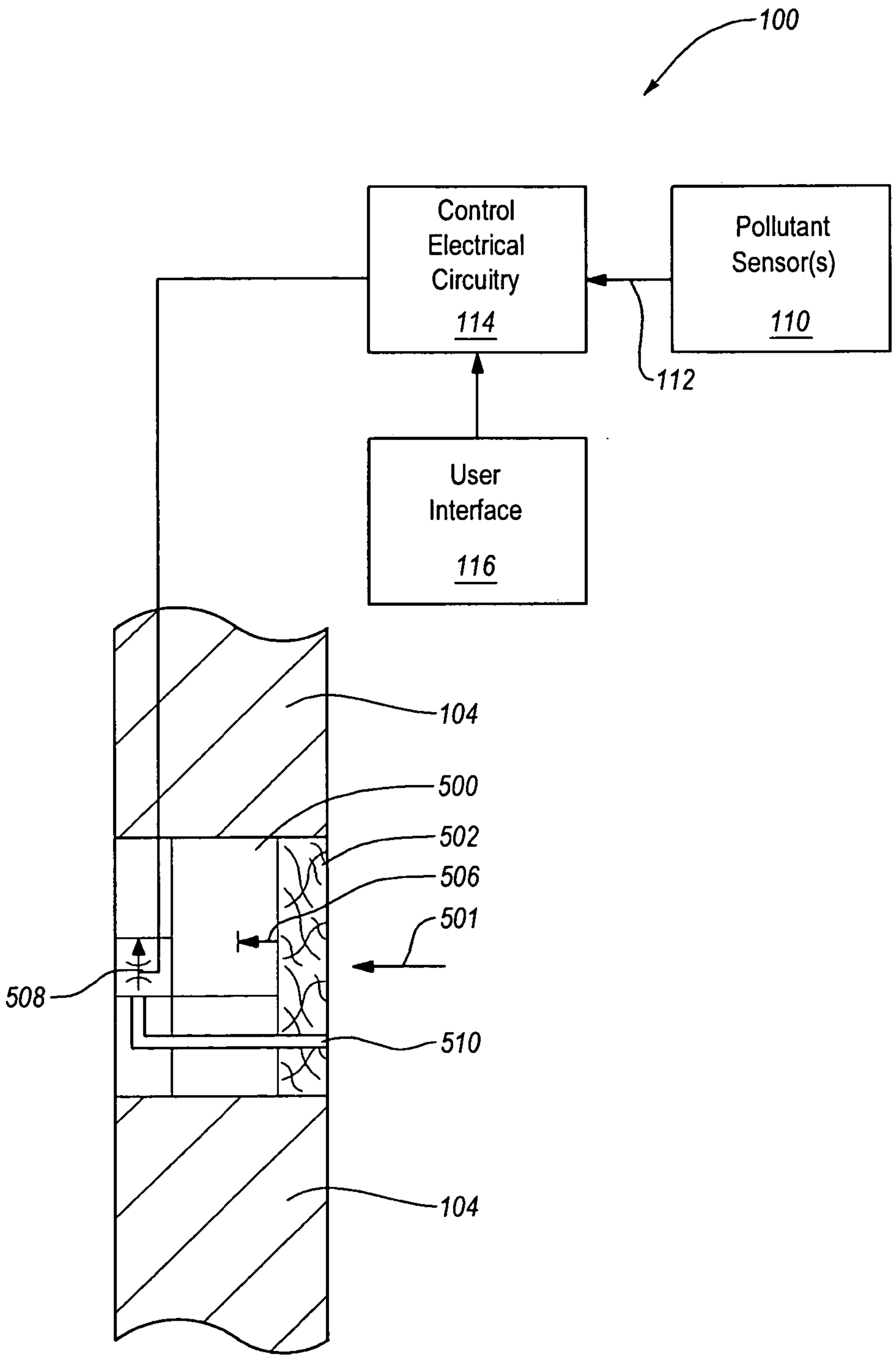
FIG. 5 is a schematic partial cross-sectional view of an embodiment of the air-treatment mask system shown in FIG. 1 taken along line 2-2 thereof in which the wearable air-treatment mask includes an auxiliary air chamber for storing incoming air therein that has been treated.

FIG. 5 is a schematic partial cross-sectional view of an embodiment of the air-treatment mask system 100 in which the mask body 104 of the wearable air-treatment mask 102 includes an auxiliary air chamber 500 for storing incoming air therein that has been treated. In the illustrated embodiment shown in FIG. 5, the at least one controllable air-treatment device 106 is configured as a passive air filter 502, but one or more of any of the active air-treatment devices disclosed herein may also be employed alternatively or additionally. For example, the passive air filter 502 may include at least one of a fibrous filter, activated charcoal, or a zeolite-based filter.

The passive air filter 502 is in fluid communication with a one-way valve 506 so that ambient air may pass through to the one-way valve 506 as incoming air to the auxiliary air chamber 500. The one-way valve 506 is configured to only allow incoming air breathed by the user and filtered by the passive air filter 502 to flow into the auxiliary air chamber 500 for storage. A flow control valve 508 (e.g., an electronically-controlled valve) is provided that is in fluid communication with the auxiliary air chamber 500, which is controlled by the control electrical circuitry 114. Although not shown, a battery may power the at least one pollutant sensor 110, the control electrical circuitry 114, and the flow control valve 508.

In operation, the control electrical circuitry 114 directs the flow control valve 508 to open and close periodically so that only incoming air that has been filtered by the passive air filter 502 is delivered to the user for breathing. The timing of the repeated open and closing of the flow control valve 508 is selected so that when the user exhales, the flow control valve 508 directs the exhalation air through a fluid conduit 510 in fluid communication with the flow control valve 508 that passes through the mask body 102. By directing the exhalation air through the fluid conduit 510, the exhalation air does not fill the auxiliary air chamber 500, which is generally only for treated incoming air. In an embodiment, incoming air includes ambient air that is treated by the passive air filter 502.

The control electrical circuitry 114 may selectively direct the flow control valve 508 to open and close in a controlled manner generally in phase with the user's inhalation and exhalation responsive to the one or more signals 112 output by the at least one pollutant sensor 110. For example, the control electrical circuitry 114 may selectively open and close the flow control valve 508 to allow substantially only the filtered incoming air stored in the auxiliary chamber 500 to flow through the flow control valve 508 for breathing by the user responsive to the one or more signals 112 indicating that pollutants (e.g., chemical or particulate pollutants) are present in the ambient air at a threshold pollutant concentration level. If the one or more signals 112 output by the at least one pollutant sensor 110 indicates that the incoming air is substantially free of airborne pollutants (e.g., select airborne pollutants) or the airborne pollutants are below a threshold pollutant concentration level, the control electrical circuitry 114 may maintain the flow control valve 508 in a position so that the user may breathe unfiltered incoming air through the fluid conduit 510.

The user interface 116 enables the user to select specific operational characteristics by which the flow control valve 508 operates. For example, in an embodiment, the user interface 116 and the control electrical circuitry 114 may be configured so that the user can select a threshold pollutant concentration level below which the control electrical circuitry 114 controls the flow control valve 508 so that the user may breathe unfiltered ambient air through the fluid conduit 5100.

Figure 6:
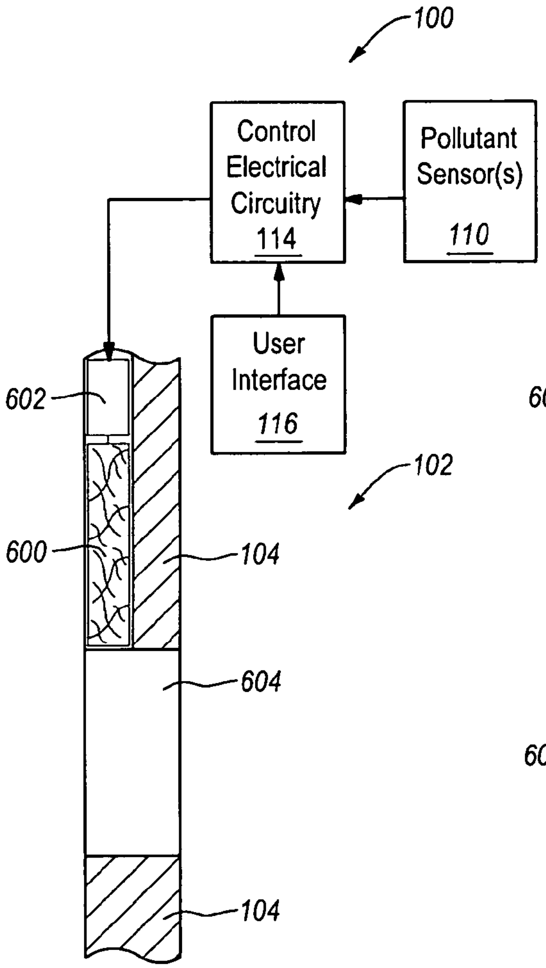
FIG. 6 is a schematic partial cross-sectional view of an embodiment of the air-treatment mask system shown in FIG. 1 taken along line 2-2 thereof in which the wearable air-treatment mask includes at least one controllable air-treatment device deployable by at least one actuator, with the at least one controllable air-treatment device shown in the un-deployed position.

FIG. 6 is a schematic partial cross-sectional view of an embodiment of the air-treatment mask system 100 in which the wearable air-treatment mask 102 includes at least one controllable air-treatment device 600 configured as any of the disclosed passive air filters that is deployable by at least one actuator 602. The at least one actuator 602 may be configured as at least one of a piezoelectric actuator, a magnetically-driven actuator, an electrostatically-driven actuator, a shape memory alloy actuator, or other suitable actuator. Although not shown, a battery may power the at least one pollutant sensor 110, the control electrical circuitry 114, and the at least one actuator 602.

FIG. 6 shows the at least one controllable air-treatment device 600 in the un-deployed position. In the un-deployed position, the passive air filter 600 may be stored within the mask body 102 so that a breathing port 604 that extends through the mask body 102 is substantially unobstructed by the passive air filter 600. When the one or more signals 112 output to the control electrical circuitry 114 by the at least one pollutant sensor 110 indicates that the ambient air is substantially free of airborne pollutants (e.g., select airborne pollutants) or the airborne pollutants are below a threshold pollutant concentration level, the control electrical circuitry 114 does not direct the at least one actuator 602 to deploy the passive air filter 600.

Figure 7:
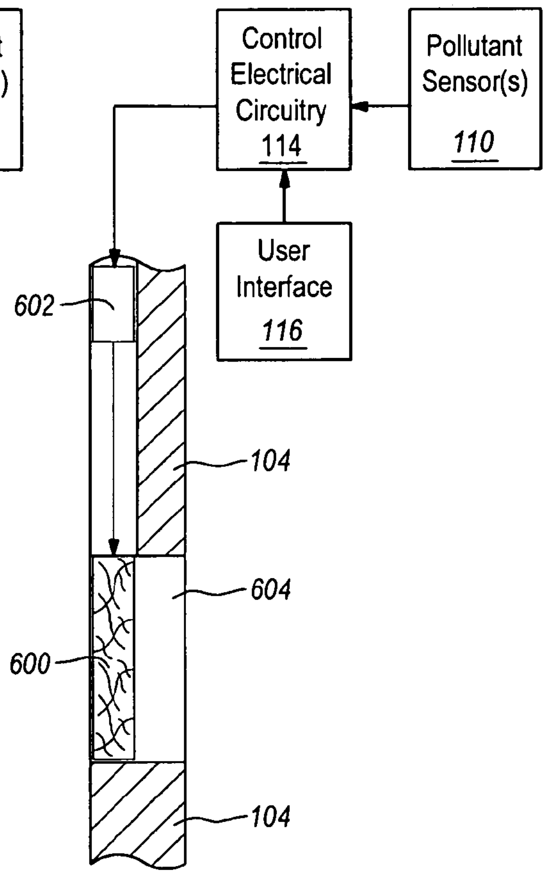
FIG. 7 is a schematic partial cross-sectional view of the air-treatment mask system shown in FIG. 6, with the at least one controllable air-treatment device shown in the deployed position.

As shown in FIG. 7, when the one or more signals 112 output to the control electrical circuitry 114 by the at least one pollutant sensor 110 indicates that the ambient air includes certain airborne pollutants or that the airborne pollutants are above a threshold pollutant concentration level, the control electrical circuitry 114 directs the at least one actuator 602 to physically move the passive air filter 600 so that the passive air filter 600 is deployed to obstruct the breathing port 604. When the passive air filter 600 is deployed, the ambient air breathed by the user is filtered by the passive air filter 600 as incoming air prior to breathing. When the one or more signals 112 output to the control electrical circuitry 114 by the at least one pollutant sensor 110 indicates that the ambient air is substantially free of airborne pollutants (e.g., select airborne pollutants) or the airborne pollutants are below a threshold pollutant concentration level, the control electrical circuitry 114 may direct the at least one actuator 602 to physically retract the passive air filter 600 to the un-deployed position shown in FIG. 6.

In an embodiment, the passive air filter 600 may be tailored for filtering specific pollutants. In an embodiment, the passive air filter 600 includes multiple different passive air filters, with each of the different passive air filters configured to selectively filter different pollutants. For example, one of the passive air filters may be configured to filter certain airborne particles, while another passive air filter may be configured to filter certain chemicals. The different filter selectivity may be based on pore size, surface configuration, fiber composition, or other selected physical or chemical property of the passive air filter.

The user interface 116 enables the user to select specific operational characteristics by which the at least one actuator 602 is controlled. In an embodiment, the user interface 116 and the control electrical circuitry 114 may be configured so that the user can select a threshold pollutant concentration level above which the control electrical circuitry 114 directs the at least one actuator 602 to deploy the passive air filter 600. In an embodiment, the user interface 116 and the control electrical circuitry 114 may be configured so that the user can select which certain types of airborne pollutants will cause the control electrical circuitry 114 to direct the at least one actuator 602 to deploy the passive air filter 600.

Figure 8:
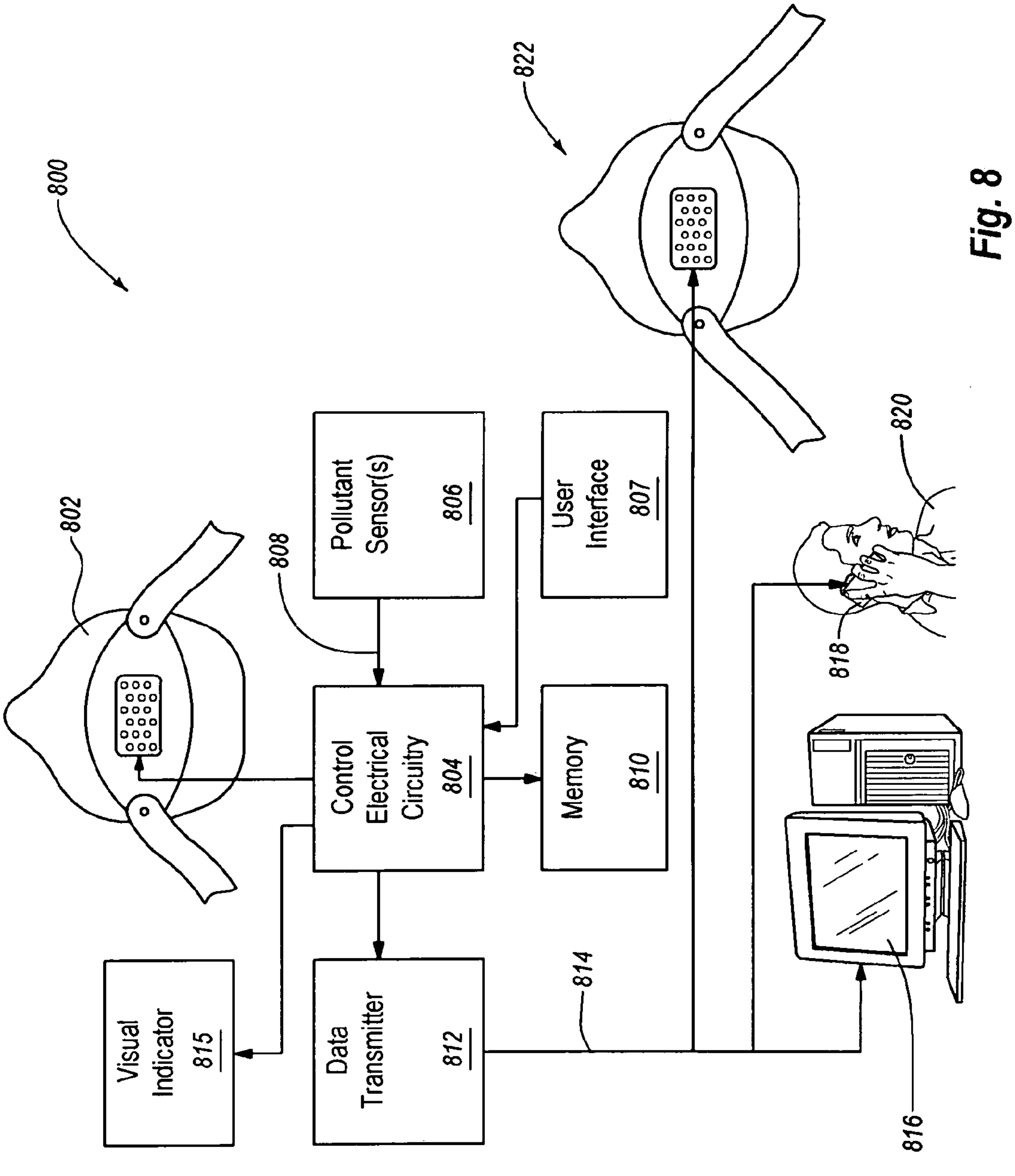
FIG. 8 is a schematic plan view of an embodiment of an air-treatment mask system configured to transmit pollutant information or other mask operating information to a third party or another device.

FIG. 8 is a diagrammatic view of an embodiment of an air-treatment mask system 800 configured to transmit pollutant information to a third party or another device. The air-treatment mask system 800 includes at least one wearable air-treatment mask 802 in association with control electrical circuitry 804 and at least one pollutant sensor 806 that outputs one or more signals 808 encoding pollutant data to the control electrical circuitry 804 responsive to sensing a pollutant level in ambient air. A user interface 807 (e.g., a computer touchscreen, keypad, or other computing device, etc.) for inputting user input may be provided, which may be operably coupled to the control electrical circuitry 804. The user interface 807 enables the user to select specific operational characteristics by which at least one controllable air-treatment device of the wearable air-treatment mask 802 is controlled. The at least one wearable air-treatment mask 802, the control electrically circuitry 804, the at least one pollutant sensor 806, and the user interface 807 may be configured as any of the previously described air-treatment mask system embodiments, such as shown and described in FIGS. 1-7.

In an embodiment, memory 810 is provided that includes memory electrical circuitry (e.g., memory electrical circuitry incorporated in a memory module), which is operably coupled to the control electrical circuitry 804 or to the at least one pollutant sensor 806. For example, the memory 810 may store the pollutant data encoded in the one or more signals 808 or operational characteristics about the wearable air-treatment mask 800 such as filtering or treatment operations performed by a controllable air-treatment device of the wearable air-treatment mask 800.

In an embodiment, a data transmitter 812 is provided that is operably coupled to the control electrical circuitry 804. The data transmitter 812 is coupled to the control electrical circuitry 804 to receive information related to the pollutant data encoded in the one or more signals 808 therefrom or information related to the wearable air-treatment mask 802 such as filtering or treatment operations performed by the at least one controllable air-treatment device of the wearable air-treatment mask 802, and transmit the one or more signals 808 as one or more transmitted data signals 814 that encode such information. For example, the data transmitter 812 may be configured as a radio-frequency data transmitter, an optical data transmitter (e.g., emitting infrared or visible light), a physical electrical interface (e.g., a USB plug) configured to allow transmission of the one or more transmitted data signals 814 to a correspondingly configured electrical interface (e.g., a USB plug) of another device, or other suitable data transmitter.

The data transmitter 812 may transmit the one or more transmitted data signals 814 to another device, such as at least one of a personal computer 816, a portable device 818 (e.g., a cell phone) of another person 820, or to another wearable air-treatment mask 822 that is configured the same or similarly to the wearable air-treatment mask 802 or any of the disclosed air-treatment mask systems. In an embodiment, the another device may be associated with a doctor, a public health official, or other person of interest. In an embodiment, the transmission of the one or more transmitted data signals 814 may be temporally spaced so that multiple transmissions of the one or more transmitted data signals 814 occur spaced over time so that, for example, the pollutant levels can be tracked over time. In an embodiment, the transmission of the one or more transmitted data signals 814 may occur over multiple regions. For example, the transmission of the one or more transmitted data signals 814 may occur when a location sensor embedded in or associated with the control electrical circuitry 802 detects that the user has changed locations over a selected distance.

As an alternative to or in addition to employing the data transmitter 812 for reporting operational and pollutant data to a third party or another device, a visual indicator 815 may be provided that is operably coupled to the control electrical circuitry 804. For example, the visual indicator 815 may be a light emitting device, such as one or more LEDs. The visual indicator 815 may be mounted or integrated with the mask body of the wearable air-treatment mask 802. In operation, the control electrical circuitry 804 may direct the visual indicator 815 to output light responsive to the one or more signals 808 indicating that airborne pollutants are present in the air above a threshold pollutant concentration level, responsive to the one or more signals 808 indicating that specific types of airborne pollutants are present in the air, or responsive to other suitable pollutant information. In an embodiment, the third party includes, for example, a doctor, user, insurance provider, public health facility, or other health care facility or provider.

In an embodiment, an alarm may be used alternatively or additionally to the visual indicator 815. For example, the alarm may include an audible alarm that generates a human audible sound responsive to the one or more signals 808 indicating that airborne pollutants are present in the air above a threshold pollutant concentration level, responsive to the one or more signals 808 indicating that specific types of airborne pollutants are present in the air, or responsive to other suitable pollutant information. The audible alarm or the visual indicator 815 may be used to alert the user to put on and deploy the wearable air-treatment mask 802.

Figure 9:
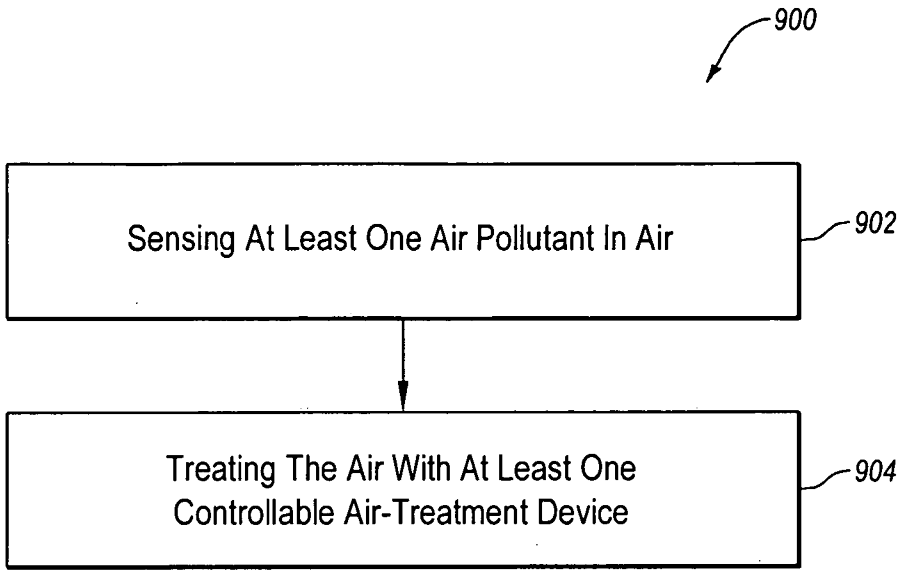
FIG. 9 is a flow diagram of an embodiment of a method for treating ambient air with an air-treatment mask system to thereby result in treated incoming air.

FIG. 9 is a flow diagram of an embodiment of a method 900 for treating ambient air with an air-treatment mask system, such as any of the air-treatment mask systems disclosed herein. The method 900 includes an act 902 of sensing at least one air pollutant in the ambient air to be breathed by the user using at least one pollutant sensor. For example, the at least one pollutant sensor may include any of the pollutant sensors described above for the at least one pollutant sensor 110 for sensing airborne particles or chemical pollutants. Furthermore, the at least one pollutant sensor may be located remote from the wearable air-treatment mask or physically integrated with the wearable air-treatment mask. The method 900 further includes an act 904 of treating incoming air with at least one controllable air-treatment device of a wearable air-treatment mask to result in treated incoming air responsive to the sensing the at least one air pollutant. For example, the wearable air-treatment mask may be configured as any of the wearable air-treatment masks shown in FIGS. 1-7. The act 904 may be performed responsive to the pollutant sensed by the at least one pollutant sensor being transmitted to control electrical circuitry of the wearable air-treatment mask.

In an embodiment, the act 900 may include filtering or at least partially neutralizing (e.g., sterilizing) the incoming air with the at least one controllable air-treatment device. For example, the act 900 may include passively or actively filtering the incoming air with the at least one controllable air-treatment device.

In an embodiment, the method 900 may further include deploying the at least one controllable air-treatment device responsive to the sensing the at least one air pollutant in act 902. For example, the at least one controllable air-treatment device may be deployed and un-deployed via at least one actuator as shown and described in FIGS. 6 and 7.

In an embodiment, the method 900 may further include an act of transmitting one or more data signals encoding information related to the sensed at least one air pollutant or operational characteristics of the wearable air-treatment mask. For example, the one or more data signals may be transmitted to a third party or another device such as another air-treatment mask system.

Figure 10:
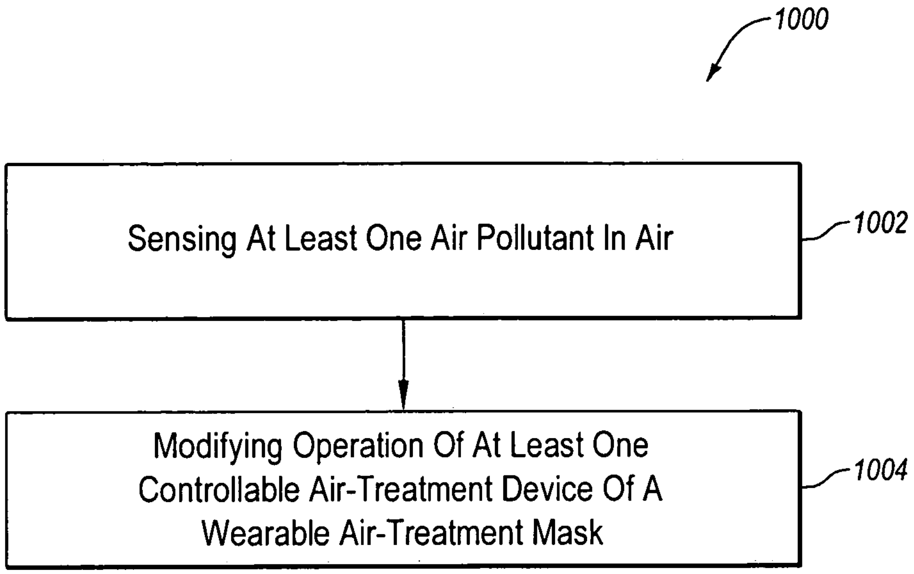
FIG. 10 is a flow diagram of an embodiment of a method for operating at least one controllable air-treatment device of a wearable air-treatment mask.

FIG. 10 is a flow diagram of an embodiment of a method 1000 for operating at least one controllable air-treatment device of a wearable air-treatment masks, such as any of the air-treatment masks and mask systems disclosed herein. The method 1000 includes an act 1002 of sensing at least one air pollutant in the ambient air to be breathed by the user with at least one pollutant sensor. The method 1000 further includes an act 1004 of modifying operation of the at least one controllable air-treatment device of the wearable air-treatment mask responsive to the sensing the at least one air pollutant.

In an embodiment, the act 1004 includes deploying or un-deploying the at least one controllable air-treatment device for treating the ambient air to thereby result in treated incoming air for breathing by the user. In an embodiment, the act 1004 includes preventing the at least one controllable air-treatment device from treating the incoming air.

In an embodiment, the method 1000 further includes treating the incoming air using the at least one controllable air-treatment device. For example, treating the incoming air may include at least partially neutralizing (e.g., sterilizing) the ambient air to transform the ambient air to at least partially neutralized incoming air to be breathed by the user, or filtering the ambient air to transform the ambient air to filtered incoming air to be breathed by the user.

In an embodiment, the devices, systems, or methods described herein are applicable for stroke prevention.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. An air-treatment mask system, comprising:

a wearable air-treatment mask including, a mask body including a face-securing member; and at least one controllable air-treatment device supported by the mask body, the at least one controllable air-treatment device configured to treat incoming air;

at least one pollutant sensor configured to sense ambient air for a presence of a plurality different types of pollutants therein and further configured to output one or more signals responsive to the sensing; and control electrical circuitry operably coupled to the at least one controllable air-treatment device and the at least one pollutant sensor, the control electrical circuitry configured to direct the at least one controllable air-treatment device to selectively treat at least one of the plurality of different types of pollutants responsive to receiving the one or more signals from the at least one pollutant sensor.

2. The air-treatment mask system of claim 1, wherein the wearable air-treatment mask includes the at least one pollutant sensor.

3. The air-treatment mask system of claim 1, wherein the wearable air-treatment mask is remote from the at least one pollutant sensor.

4. The air-treatment mask system of claim 1, wherein the at least one pollutant sensor is configured to be worn by the user.

5. The air-treatment mask system of claim 1, wherein the at least one controllable air-treatment device includes at least one air filter configured to filter the incoming air.

6. The air-treatment mask system of claim 5, wherein the at least one air filter includes at least one passive air filter.

7. The air-treatment mask system of claim 6, wherein the at least one passive air filter includes at least one of a fibrous filter, activated charcoal, or a zeolite-based filter.

8. The air-treatment mask system of claim 5, wherein the at least one air filter includes at least one active air filter controlled by the control electrical circuitry and configured to selectively filter the incoming air.

9. The air-treatment mask system of claim 8, wherein the at least one active air filter includes at least one of an electrostatic filter, an optical filter, or a chemical-reagent-based filter.

10. The air-treatment mask system of claim 1, wherein the at least one controllable air-treatment device is configured to filter airborne particles.

11. The air-treatment mask system of claim 1, wherein the at least one controllable air-treatment device is configured to at least partially neutralize one or more chemical pollutants.

12. The air-treatment mask system of claim 11, wherein the one or more chemical pollutants include at least one of ozone, nitrogen oxide, sulfur oxide, or pathogens.

13. The air-treatment mask system of claim 1, wherein the at least one pollutant sensor includes at least one particle sensor configured to sense airborne particles in the ambient air.

14. The air-treatment mask system of claim 1, wherein the at least one pollutant sensor includes at least one chemical sensor configured to sense one or more chemical pollutants in the ambient air.

15. The air-treatment mask system of claim 1, wherein the at least one pollutant sensor is configured to wirelessly communicate the one or more signals to the control electrical circuitry.

16. The air-treatment mask system of claim 1, wherein the at least one pollutant sensor is electrically or optically coupled to the control electrical circuitry to communicate the one or more signals thereto.

17. The air-treatment mask system of claim 1, wherein the control electrical circuitry is configured to determine when to utilize the at least one controllable air-treatment device.

18. The air-treatment mask system of claim 17, wherein the wearable air-treatment mask includes at least one actuator configured to deploy the at least one controllable air-treatment device responsive to the control electrical circuitry determining that the at least one controllable air-treatment device is to be deployed.

19. The air-treatment mask system of claim 1, wherein the wearable air-treatment mask includes at least one valve configured to control a flow of the incoming air to the at least one controllable air-treatment device.

20. The air-treatment mask system of claim 1, wherein control electrical circuitry is configured to control treatment strength of the at least one controllable air-treatment device.

21. The air-treatment mask system of claim 1, wherein the wearable air-treatment mask includes at least one valve operably coupled to the control electrical circuitry, the control electrical circuitry configured to control the operation of the at least one valve to control delivery of the treated air to the user.

22. The air-treatment mask system of claim 1, wherein the control electrical circuitry is configured to direct the at least one controllable air-treatment device to treat the incoming air based on certain criteria.

23. The air-treatment mask system of claim 1, wherein the control electrical circuitry is programmable for tailoring the operation of the at least one controllable air-treatment device to a specific condition.

24. The air-treatment mask system of claim 1, further comprising a data transmitter coupled to the control electrical circuitry, the data transmitter configured to transmit information at least related to pollutant data encoded in the one or more signals.

25. The air-treatment mask system of claim 24, wherein the data transmitter is configured to wirelessly transmit the information.

26. The air-treatment mask system of claim 24, wherein the data transmitter is configured to transmit the information via an electrical interface.

27. The air-treatment mask system of claim 24, wherein the control electrical circuitry is configured to direct the data transmitter to transmit the information to a third party or another device.

28. The air-treatment mask system of claim 27, wherein the another device includes another air-treatment mask system.

29. The air-treatment mask system of claim 1, further comprising a data transmitter coupled to the control electrical circuitry, the control electrical circuitry configured to direct the data transmitter to transmit information related to the operation of the at least one controllable air-treatment device.

30. The air-treatment mask system of claim 29, wherein the control electrical circuitry is configured to direct the data transmitter to transmit the information to a third party or another device.

31. The air-treatment mask system of claim 30, wherein the another device includes another air-treatment mask system.

32. The air-filtration mask system of claim 1, further comprising a memory module configured to store pollutant data encoded in the one or more signals from the at least one pollutant sensor.

33. The air-filtration mask system of claim 1, wherein the wearable air-treatment mask includes an auxiliary air chamber configured to store air that has been treated by the at least one controllable air-treatment device.

34. A method of treating ambient air to be breathed by a user, the method comprising:

sensing a plurality of different types of pollutants in the ambient air to be breathed by the user using at least one pollutant sensor; and responsive to the sensing the plurality of different types of pollutants, selectively treating at least one of the plurality of different types of pollutants in the incoming air to be breathed by the user with at least one controllable air-treatment device of a wearable air-treatment mask.

35. The method of claim 34, wherein sensing a plurality of different types of pollutants in the ambient air to be breathed by the user using at least one pollutant sensor includes sensing airborne particles in the ambient air to be breathed by the user.

36. The method of claim 34, wherein sensing a plurality of different types of pollutants in the ambient air to be breathed by the user using at least one pollutant sensor includes sensing one or more chemical pollutants in the ambient air to be breathed by the user.

37. The method of claim 34, wherein sensing a plurality of different types of pollutants in the ambient air to be breathed by the user using at least one pollutant sensor includes sensing at least one pollutant with the at least one pollutant sensor that is remote from the wearable air-treatment mask.

38. The method of claim 34, wherein sensing a plurality of different types of pollutants in the ambient air to be breathed by the user using at least one pollutant sensor includes sensing at least one pollutant with the at least one pollutant sensor that is included the wearable air-treatment mask.

39. The method of claim 34, further comprising transmitting information related to the plurality of different types of pollutants sensed to control electrical circuitry of the wearable air-treatment mask.

40. The method of claim 34, wherein treating incoming air to be breathed by the user with at least one controllable air-treatment device of a wearable air-treatment mask includes filtering the incoming air with the at least one controllable air-treatment device.

41. The method of claim 34, wherein treating incoming air to be breathed by the user with at least one controllable air-treatment device of a wearable air-treatment mask includes sterilizing the incoming air with the at least one controllable air-treatment device.

42. The method of claim 34, wherein treating incoming air to be breathed by the user with at least one controllable air-treatment device of a wearable air-treatment mask includes passively filtering the incoming air with the at least one controllable air-treatment device.

43. The method of claim 34, wherein treating incoming air to be breathed by the user with at least one controllable air-treatment device of a wearable air-treatment mask includes actively filtering the incoming air with the at least one controllable air-treatment device.

44. The method of claim 34, further comprising deploying the at least one controllable air-treatment device responsive to the sensing the at least one of the plurality of different types of pollutants.

45. The method of claim 34, wherein treating incoming air to be breathed by the user with at least one controllable air-treatment device of a wearable air-treatment mask includes treating the incoming air based on certain treatment criteria.

46. The method of claim 34, further comprising transmitting one or more data signals encoding information related to the at least one of the plurality of different types of pollutants so sensed.

47. The method of claim 46, wherein transmitting one or more data signals encoding information related to the at least one of the plurality of different types of pollutants so sensed includes transmitting the one or more data signals to a third party or another device.

48. The method of claim 47, wherein the another device includes another air-treatment mask system.

49. The method of claim 34, further comprising transmitting one or more data signals encoding information related to the operation of the at least one controllable air-treatment device.

50. The method of claim 49, wherein transmitting one or more data signals encoding information related to the operation of the at least one controllable air-treatment device includes transmitting the one or more data signals to a third party or another device.

51. The method of claim 50, wherein the another device includes another air-treatment mask system.

52. The method of claim 34, further comprising storing data related to the at least one of the plurality of different types of pollutants so sensed.

53. The method of claim 34, further comprising storing the treated air in an auxiliary chamber of the wearable air-treatment mask.

54. The method of claim 34, wherein storing the treated air in an auxiliary chamber of the wearable air-treatment mask includes storing the treated air in the auxiliary chamber prior to delivery to the user for breathing.

55. The method of claim 34, responsive to the sensing the at least one of the plurality of different types of pollutants, further comprising deploying the at least one controllable air-treatment device.

56. A method of operating at least one controllable air-treatment device of a wearable air-treatment mask worn by a user, the method comprising:

sensing a plurality of different types of pollutants with at least one pollutant sensor in ambient air to be breathed by the user; and responsive to the sensing at least one type of pollutant within the plurality of different types of pollutants, modifying operation of the at least one controllable air-treatment device of the wearable air-treatment mask.

57. The method of claim 56, wherein the modifying the operation of the at least one controllable air-treatment device of the wearable air-treatment mask includes un-deploying the at least one controllable air-treatment device from treating incoming air.

58. The method of claim 56, wherein the modifying the operation of the at least one controllable air-treatment device of the wearable air-treatment mask includes preventing the at least one controllable air-treatment device from treating incoming air.

59. The method of claim 56, wherein the modifying the operation of the at least one controllable air-treatment device of the wearable air-treatment mask includes deploying the at least one controllable air-treatment device to treat incoming air.

60. The method of claim 56, wherein the modifying the operation of the at least one controllable air-treatment device of the wearable air-treatment mask includes actuating the at least one controllable air-treatment device to treat incoming air.

61. The method of claim 56, wherein the modifying the operation of the at least one controllable air-treatment device of the wearable air-treatment mask includes controlling an amount of air treatment by the at least one controllable air-treatment device treats incoming air.

62. The method of claim 56, further comprising treating incoming air using the at least one controllable air-treatment device.

63. The method of claim 56, wherein treating incoming air using the at least one controllable air-treatment device includes sterilizing the incoming air to be breathed by the user.

64. The method of claim 56, wherein treating incoming air using the at least one controllable air-treatment device includes filtering the incoming air to be breathed by the user.

65. The method of claim 56, wherein the modifying the operation of the at least one controllable air-treatment device of the wearable air-treatment mask includes storing treated air in an auxiliary chamber of the wearable air-treatment mask.

66. A wearable air-treatment mask system, comprising:

a mask body including a face-securing member;

at least one controllable air treatment device supported by the mask body, the at least one controllable air treatment device configured to controllably treat incoming air;

at least one pollutant sensor configured to sense ambient air for a presence of at least one pollutant therein and further configured to output one or more signals responsive to the sensing;

control electrical circuitry operably coupled to the at least one controllable air treatment device and the at least one pollutant sensor, the control electrical circuitry configured to control operation of the at least one controllable air treatment device responsive to receiving the one or more signals from the at least one pollutant sensor; and a data transmitter coupled to the control circuitry, the data transmitter configured to transmit information at least related to pollutant data encoded in the one or more signals to at least one of a personal computer, a portable device, a third party, or another wearable air-treatment mask.

* * * * *

UNITED STATES PATENT AND TRADEMARK OFFICE

CERTIFICATE OF CORRECTION

PATENT NO. : 8,574,331 B2
APPLICATION NO. : 13/317770
DATED : November 5, 2013
INVENTOR(S) : Mahalaxmi Gita Bangera et al.

It is certified that error appears in the above-identified patent and that said Letters Patent is hereby corrected as shown below:

On the Title Page, item (75):
Line 4, change "Lowell L. Wood" to --Lowell L. Wood, Jr.--

In the Claims:

Column 19
Line 34, change "is included the wearable" to --is included with the wearable--

Signed and Sealed this
Fifth Day of August, 2014

Michelle K. Lee

Michelle K. Lee
*Deputy Director of the United States Patent and Trademark Office*